United States Patent [19]

Fujisawa et al.

[11] Patent Number: 4,483,679

[45] Date of Patent: Nov. 20, 1984

[54] COMPOUNDED THERMOPLASTICIZED ISOPRENE POLYMER RESIN FOR FILLING A DENTAL ROOT CANAL, AND METHOD OF MAKING SAME

[75] Inventors: Mutsuo Fujisawa, Musashino; Mitsuru Otani; Haruhiro Ohtsu, both of Tokyo; Tsutomu Kameda, Morioka, all of Japan

[73] Assignee: Toyo Chemical Laboratories, Inc., Tokyo, Japan

[21] Appl. No.: 445,579

[22] Filed: Nov. 30, 1982

[30] Foreign Application Priority Data

Jan. 21, 1982 [JP] Japan ................................. 57-7774

[51] Int. Cl.$^3$ .............................................. A61K 6/08
[52] U.S. Cl. ................................... 433/228; 106/35; 106/230; 106/241; 523/116; 524/62; 524/77
[58] Field of Search ................. 106/35, 230, 231, 241; 433/228; 523/116; 524/62, 77

[56] References Cited

U.S. PATENT DOCUMENTS 2,077,396 4/1937 Charch et al. ..................... 106/230

OTHER PUBLICATIONS

Journal of Endodontics, vol. 3, No. 5, May 1977, pp. 168-174, Yee et al.

Japanese patent application Ser. No. 51-111602, filed Sep. 17, 1976, by Toyo Chemical Laboratories, Inc. (English Translation of Title and Claim 1 provided as well).

Primary Examiner—Lorenzo B. Hayes
Attorney, Agent, or Firm—Fleit, Jacobson, Cohn & Price

[57] ABSTRACT

The invention is directed to a compounded thermoplasticized gutta percha or balata and isoprene polymer resin, for filling a dental root canal in an efficient and convenient manner, and a method for preparing the same.

The compounded resin includes gutta percha or balata and isoprene polymer and compounding materials including paraffin wax, adapted to compound the gutta percha or balata and isoprene polymer such that they plasticize at a relatively low temperature in the range of 40° C. to 60° C. The use of gutta percha or balata and isoprene polymer, and the relatively low plasticizing temperature, enable the compounded resin to be injected into a prepared dental root canal for filling thereof in an efficient and convenient manner.

The method for preparing the compounded resin includes combining, heating and mixing gutta percha or balata and isoprene polymer and the compounding materials to a relatively low temperature in the range of 40° C. to 60° C., at which temperature the compounded materials plasticize, to form the compounded resin.

9 Claims, No Drawings

COMPOUNDED THERMOPLASTICIZED ISOPRENE POLYMER RESIN FOR FILLING A DENTAL ROOT CANAL, AND METHOD OF MAKING SAME

BACKGROUND OF THE INVENTION

1 Field of the Invention

The invention relates generally to a material for filling a dental root canal and a method for preparing same. Specifically, the invention relates to a compounded thermosplasticized, injectable resin for filling a dental root canal, and a method of making same.

2 Description of the Prior Art

Materials presently known for filling a dental root canal include pastes, gutta percha cones, and thermosplasticized gutta percha.

Pastes consist generally of materials in the calcium hydroxide series, used by filling the root canal therewith. Such pastes, however, are generally difficult and inconvenient to use, and are therefore not desirable for use in dental root canal filling.

Gutta percha cones are the most widely used dental root canal filling material. They consist of thin, solid rods of gutta percha, a purified, coagulated, milky exude of various trees. In rod form, however, it is very difficult to use gutta percha to make a complete seal to the tip of the root canal because the length and size of the root canal is different for each patient. For example, molars with curved root canals require advanced and different techniques for inserting gutta percha cones up to the root canal tip, even after root canal enlargement.

In preparing a dental root canal for filling with a material such as gutta percha, the tooth pulp is first extirpated from the tooth. The length of the root canal is then measured, up to the clinical apical foramen, by a meter, or by a compensated measurement directly from an X-ray. An insertion needle known as a reamer is then used to enlarge the root canal, and a dental file is then used to form an apical seat approximately 1 to 2 millimeters inside the apical foramen. The shaped root canal is then cleansed and sterilized.

In filling the dental root canal, prepared as described above, by using gutta percha cones, a gutta percha cone of a size larger than the last dental file used to form the apical seat, is pressed laterally to the root canal wall by an instrument known as a spreader, making room for several further gutta percha cones which are then inserted for packing. After treatment, X-rays are taken to determine whether the root canal is packed.

However, after filling the dental root cannal by using gutta percha cones, patients frequently complain of pain, indicating improper healing and filling, although the X-rays had indicated complete packing. This problem is caused in part by imperfect packing of the the root canal, resulting from floating of the main gutta percha cone from the apical foramen, and from imprecise shaping of the root canal. In shaping the root canal by filling, the shape formed thereby does not precisely coincide with the shape of the gutta percha cones, whereby dead space areas are formed, which becomes sources of secondary infections. Further, due to lateral pressures exerted after filling, the gutta percha cones frequently become separated from the foramen apex.

Gutta percha cones are also used in heated form in several root canal filling methods.

In a root canal filling method known as the lateral condensation method, hard gutta percha is inserted and melted at the top of the tooth downward toward the tip, causing lateral flow and softening. However, the gutta percha must be heated to a relatively high temperature to flow freely, and must further be removed, reheated, and reinserted, which, aside from causing discomfort, and lengthy treatment, further causes rapid cooling. Coupled with the syringe pressurization, this method frequently results in fracturing of the filling and the tooth. Further, gutta percha is also absorbed in the root canal, and prevented from being absorbed in the surrounding tissues, when pushed out of the apex hole, causing harmful side effects.

It has been considered that heat could be applied to gutta percha cones for use in a root canal filling method known as the vertical condensation method. However, since gutta percha cones were developed for use in the lateral condensation method, they contain natural rubber and resin, to maintain lateral strength, which have a relatively high plasticity temperature, in the range of 80° C. to 90° C., which operating temperature would give a patient considerable pain, or break a filling or tooth by exerting excessive vertical pressure due to rapid cooling of the material.

Thermoplasticized gutta percha has been developed relatively recently, and is injectable in heated form to mold to the prepared root canal.

In using thermoplasticized gutta percha, it is heated to a temperature sufficiently high to render it sufficiently plasticized, then injected by syringe into the prepared dental root canal which it fills under pressure, and is then permitted to cool and harden.

One presently known form of thermoplasticized gutta percha consists of gutta percha cones to which a thermoplasticizing agent has been added. This form has been described generally in an article by Dr. Fulton S. Yee et. al., "Three-Dimensional Obturation of the Root Canal using Injection-Molded, Thermoplasticized Dental Gutta-Percha", 3 Journal of Endodontics, No. 5, pages 168–174 (May 1977). The thermoplasticized gutta percha material described generally therein, however, must be heated to a temperature of 160° C. to generate unrestrained flow for use as an injectable filling, which temperature is too high for manual handling and use on patients in clinical situations.

The other presently known form of thermoplasticized gutta percha consists of gutta percha resin, compounded with other materials to plasticize at a temperature in the range of 50° C. to 70° C., which has been described in Japanese patent application serial No. 51-111602, filed Sept. 17, 1976, for "A Dental Material for Root Canal Filling which is Filled by Means of a Syringe", By Toyo Chemical laboratories, Inc., Tokyo, Japan. However, the thermoplasticized gutta percha material described therein is not of optimum efficiency and convenience, in that it is gutta percha based, and must be heated to a temperature not optimallly suited for routine clinical use by technicians.

SUMMARY OF THE INVENTION

The invention comprises a compounded thermoplasticized gutta percha or a mixture of balata and isoprene polymer resin for filling a dental root canal, and a method for preparing same. The resin and method of the invention overcome the problems described above as well as other, and provide an optimal combination of durability and relatively low softening temperature for dental root canal filling.

The compounded isoprene polymer resin of the invention includes gutta percha or balata and isoprene polymer, and compounding materials, including paraffin wax, adapted to compound the gutta percha or balata and isoprene polymer such that the compounded resin plasticizes at a relatively low operating temperature in the range of 40° C. to 60° C. The compounded resin includes further compounding materials, including white wax and bees wax, and further resin-forming materials, including zinc oxide and zinc sulfide, as well as barium sulfate.

The use of gutta percha or balata and isoprene resin, and the relatively low temperature at which the compounded isoprene polymer resin plasticizes, enables such compounded resin to be injected into a prepared root canal for filling thereof in a complete and durable manner. It further enables use of the vertical condensation filling method, in which the compounded resin is injected in softened form, and condensed, from the tip of the tooth vertically, in a relatively short period of time. Further, any material coming out of the apex hole is absorbed in the tissues with which it comes into contact. The compounded resin still further prevents patient from discomfort during use thereof, or prevents rapid cooling or fracturing of the filling, or absorption of the compound resin in the root canal.

The method for preparing the compounded resin includes the steps of combining, heating, and mixing the gutta percha or balata and isoprene polymer and compounding materials, efficiently and conveniently, in the relatively low operating temperature range of 40° C. to 60° C., at which the compounded resin softens, plasticizes, and forms.

DESCRIPTION OF THE PREFERRED EMBODIMENT

In the preferred embodiment of the invention, a compounded thermoplasticized gutta percha or balata and isoprene polymer resin, for use in the filling a prepared dental root canal, and a method of preparing the compounded resin, are described as follows:

The preferred compounded resin comprises gutta percha or balata and isoprene polymer, preferably of the transform type 1,4 bond and 3,4 bond. The materials for compounding the isoprene polymer such that the compounded resin plasticizes in the relatively low preferred range of 40° C. to 60° C., preferably includes paraffin wax, having a melting point in the range of 40° C. to 60° C., for lowering the resin softening temperature, and further compounding materials. White wax, known as Japan wax, is included, and is adapted to improve the viscosity of the resin. Bees wax is likewise included for improved resin viscosity. Zinc oxide is included to provide a cementitious characteristic to the resin. Zinc sulfide is included as a cement clarifier for the resin. Barium sulfate is included to function as an X-ray contrast medium.

The following are examples of the elements and their parts-by-weight for various resins compounded in accordance with the invention described herein: Gutta percha or balta and isoprene polymer are called hereinafter isoprene polymer.

EXAMPLE 1

| ELEMENT | PART BY WEIGHT |
| --- | --- |
| A. Isoprene Polymer | 10 |
| B. Paraffin Wax (melting point 46° C.) | 12 |
| C. White Wax | 0.4 |
| D. Bees' Wax | 4 |
| E. Zinc Oxide | 28 |
| F. Zinc Sulfide | 12 |
| G. Barium Sulfate | 28 |

EXAMPLE 2

| ELEMENT | PART BY WEIGHT |
| --- | --- |
| A. Isoprene Polymer | 9.6 |
| B. Paraffin Wax (melting point 54° C.) | 11 |
| C. White Wax | 0.5 |
| D. Bees Wax | 2.7 |
| E. Zinc Oxide | 30 |
| F. Zinc Sulfide | 11.4 |
| G. Barium Sulfate | 26.6 |

EXAMPLE 3

| ELEMENT | PARTS BY WEIGHT |
| --- | --- |
| A. Isoprene Polymer | 11 |
| B. Paraffin Wax (melting point 60° C.) | 10 |
| C. White Wax | 0.9 |
| D. Bees' Wax | 3 |
| E. Zinc Oxide | 32 |
| F. Zinc Sulfide | 12.9 |
| G. Barium Sulfate | 30.1 |

Example 1 is a compounded resin of the invention particularly suitable for filling the curved root canals in a multi-root tooth, such as a molar, by virtue of the softening temperature of approximately 40° C.

Example 2 is a compounded resin of the invention particularly suitable for filling the pre-molars, by virtue of the softening temperature thereof of approximately 53° C.

Example 3 is a compounded resin of the invention particularly suitable for filling an anterior tooth which has a single root and a relatively large root canal, by virtue of its softening temperature of approximately 60° C.

By virtue of the use of isoprene polymer, and the relatively low softening temperature resulting from the compounding materials, the compounded resin as described above is adapted to plasticize and soften at the relatively low temperature, preferably in the range of 40° C. to 60° C. At such temperatures, the compounded resin may be readily and comfortably handled by the dental technician performing the root canal filling treatment, the patient will experience little, if any pain of discomfort associated therewith, and the compounded resin will cool at a moderate rate, preventing filling or tooth fracture.

Further, the compounded resin above may be used in the vertical condensation filling method. In such method the compounded resin is inserted in a syringe, softened, at the softening temperature in the range of 40° C. to 60° C., and injected softened so as to flow from the tip of the tooth in a generally vertical direction, filling the entire root canal in a three-dimensional manner, in a relatively short period of time of approximately 20 seconds.

Still further, the compounded resin herein prevents absorbtion in the root canal, while enabling material coming out of the apex hole to be absorbed in the tissues which is contacts.

In the preferred method of making the compounded resin, 9.6 to 11 parts by weight of isoprene polymer is first combined with the compounding materials. The compounding materials preferably include 10 to 12 parts by weight of paraffin wax having a melting point in the range of 40° C. to 60° C., 0.4 to 0.9 parts by weight of white wax (Japan wax), 2.7 to 4 parts by weight of bees wax, 28 to 32 parts by weight of zinc oxide, 11.4 to 12.9 parts by weight of zinc sulfide, and 26.6 to 30.1 parts by weight of barium sulfate.

The above combined elements are next heated to the relatively low plasticizing temperature thereof, in the range of 40° C. to 60° C. and the combined, heated, and plasticized elements are then mixed together to form the compounded resin in a convenient and efficient manner.

Preferred embodiments of the present invention have been set forth above, for the purpose of explaining the invention. It is to be understood, however, that variations and changes may be made in such preferred embodiments, which are nevertheless within the scope and spirit of the invention, as set forth in the following claims.

We claim:

1. In a dental thermoplasticized resin composition for root canal filling which is filled by means of a syringe, the improvement comprises, as said thermoplasticized resin composition a mixture having a softening point of 40°-60° C. and consisting of:
   (a) gutta percha or a mixture of balata and isoprene polymer, and
   (b) compounding materials consisting of paraffin wax, Japan wax, bees wax, zinc oxide, zinc sulfide and barium sulfate.

2. A composition as in claim 1 in which the isoprene polymer comprises the transform type 1.4 bond and 3.4 bond isoprene polymer.

3. A resin composition as in claim 1, in which said gutta percha or mixture of balata and isoprene polymer comprises between 9.6 and 11 parts by weight.

4. A resin composition as in claim 1, in which the paraffin wax has a melting point of about 46° C.

5. A resin composition as in claim 1, in which the paraffin wax comprises between 10 parts 12 parts by weight.

6. A resin composition as in claim 1, in which the Japan wax comprises between 0.4 and 0.9 parts by weight, and the bees wax comprises between 2.7 and 4 parts by weight.

7. A resin composition as in claim 1, in which the zinc oxide comprises between 28 and 32 parts by weight, and the zinc sulfide comprises between 11.4 and 12.9 parts by weight.

8. A resin composition as in claim 1, in which the barium sulfate, comprises between 26.6 and 30.1 parts by weight.

9. A method of making a thermoplasticized gutta percha or a mixture of balata and isoprene polymer composition for filling a dental root canal, adapted to plasticize at a temperature of 40° to 60° C., comprising:
   (a) combining gutta percha or said mixture of balata and isoprene polymer and compounding materials consisting of paraffin wax, Japan wax, beeswax, zinc oxide, zinc sulfide and barium sulfate and
   (b) heating the combined gutta percha or mixture of balata and isoprene polymer resin and compounding materials to a temperature of 40° to 60° C. at which temperature the combined components plasticize.

* * * * *